(12) United States Patent
Allen et al.

(10) Patent No.: US 7,101,461 B2
(45) Date of Patent: Sep. 5, 2006

(54) METHOD AND APPARATUS FOR IMAGING A PAPER WEB

(75) Inventors: Peter J. Allen, Neenah, WI (US); Scott H. Delzer, Greenville, WI (US); Lindsay M. Brewster, Perry, OH (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/772,282

(22) Filed: Jan. 29, 2001

(65) Prior Publication Data

US 2002/0100569 A1   Aug. 1, 2002

(51) Int. Cl.
*D21F 7/00* (2006.01)
*D21F 11/02* (2006.01)
*G01N 21/89* (2006.01)

(52) U.S. Cl. ............... 162/198; 162/192; 162/252; 162/253; 162/263; 162/DIG. 11; 250/559.01; 250/559.05; 250/559.06; 250/559.08; 356/429; 356/430; 356/431; 700/127; 700/128

(58) Field of Classification Search ........ 162/252–254, 162/263, 198, 199, 262, DIG. 6, DIG. 10, 162/DIG. 11, 192; 250/559.06, 559.07, 559.08, 250/559.01, 559.04, 559.05, 339.1, 339.02, 250/339.06, 339.11, 341.7, 341.8; 356/237.1, 356/429–431, 237.2, 239.1, 239.7; 364/469.01, 364/471; 700/127–129; 382/108, 112; 73/159
See application file for complete search history.

(56) References Cited

U.S. PATENT DOCUMENTS

| | | | |
|---|---|---|---|
| 3,807,868 A | 4/1974 | Simila | |
| 4,500,968 A | 2/1985 | Bialkowski | |
| 4,644,174 A * | 2/1987 | Ouellette et al. | 250/559.01 |
| 4,760,271 A * | 7/1988 | Brenholdt | 250/559.05 |
| 4,857,747 A | 8/1989 | Bolton et al. | |
| 4,931,657 A | 6/1990 | Houston et al. | |
| 4,955,720 A | 9/1990 | Blecha et al. | |
| 5,011,573 A | 4/1991 | Niemi | |
| 5,047,652 A | 9/1991 | Lisnyansky et al. | |
| 5,068,799 A | 11/1991 | Jarrett, Jr. | |
| 5,113,454 A | 5/1992 | Marcantonio et al. | |
| 5,162,660 A | 11/1992 | Popil | |

(Continued)

FOREIGN PATENT DOCUMENTS

EP          0046058 A2    2/1982

(Continued)

OTHER PUBLICATIONS

Brochure, Piranha CT-P1, *Dalsa*, Aug. 28, 2001, 2 pages.

(Continued)

*Primary Examiner*—Eric Hug
(74) *Attorney, Agent, or Firm*—Dority & Manning, P.A.

(57) ABSTRACT

A system and process for measuring paper formation characteristics in real time is disclosed. The system comprises apparatus used in a papermaking process, and includes a rotating forming fabric having an upper and lower surface. A paper slurry is deposited upon the upper surface of the moving forming fabric to prepare a wet paper web. The wet paper web typically moves at a high rate of speed as it rides along upon the surface of the forming fabric. Light is transmitted from a light source to the surface of the wet paper web, and then reflected from the surface of the wet paper web to a camera. An image is formed corresponding to the pattern of the reflected light, and in some instances data generated from the reflected light may be compared to other values to provide a feedback loop to adjust the parameters of the papermaking process in real time.

27 Claims, 2 Drawing Sheets

U.S. PATENT DOCUMENTS

| | | |
|---|---|---|
| 5,237,181 A | 8/1993 | Kerkhoff et al. |
| 5,341,824 A | 8/1994 | Fletcher et al. |
| 5,351,308 A | 9/1994 | Kaminer et al. |
| 5,383,135 A | 1/1995 | Shofner et al. |
| 5,393,378 A * | 2/1995 | Yakabe et al. ............... 162/61 |
| 5,399,859 A | 3/1995 | Gray et al. |
| 5,472,571 A | 12/1995 | Niemi |
| 5,563,809 A | 10/1996 | Williams et al. |
| 5,572,433 A | 11/1996 | Falconer et al. |
| 5,622,602 A | 4/1997 | Yakabe et al. |
| 5,692,267 A | 12/1997 | Leifeld |
| 5,718,060 A | 2/1998 | Mori |
| 5,745,365 A | 4/1998 | Parker |
| 5,786,894 A | 7/1998 | Shields et al. |
| 5,812,404 A | 9/1998 | Hamalainen et al. |
| 5,821,990 A | 10/1998 | Rudt et al. |
| 5,822,070 A * | 10/1998 | Syre ......................... 356/419 |
| 5,853,543 A | 12/1998 | Hu et al. |
| 5,891,306 A | 4/1999 | Chase et al. |
| 5,899,959 A * | 5/1999 | Shields et al. ............... 702/35 |
| 5,928,475 A | 7/1999 | Chase et al. |
| 6,053,040 A * | 4/2000 | Callender et al. ............ 73/159 |
| 6,129,817 A * | 10/2000 | Rule, Jr. .................... 162/253 |
| 6,301,373 B1 * | 10/2001 | Bernie et al. ............... 382/108 |
| 6,743,337 B1 * | 6/2004 | Ischdonat .................. 162/198 |

FOREIGN PATENT DOCUMENTS

| | | |
|---|---|---|
| EP | 0464958 B1 | 1/1992 |
| EP | 0468538 B1 | 1/1992 |

OTHER PUBLICATIONS

Brochure, Sherlock by Coreco Imaging, Inc., 2 pages.
Brochure, The Fostec Lightlines Product Bulletin 4001, Apr. 1997, 2 pages.

* cited by examiner

METHOD AND APPARATUS FOR IMAGING A PAPER WEB

BACKGROUND OF THE INVENTION

In the manufacture of paper products, an aqueous suspension containing pulp fibers is formed. The aqueous suspension is spread over a forming surface to form a paper web. The forming surface generally includes a series of endless rotating conveyor belts formed from a porous fabric that is comprised of metal, plastic, or other suitable material. Forming fabrics are designed to facilitate the formation of the non-woven web, to transport the non-woven web, and to remove excess liquid from the web as it travels downstream. When forming low basis weight paper products, such as tissues, the non-woven web is formed between a pair of forming fabrics. In these systems, the suspension of fibers is injected between a pair of moving fabrics as the fabrics are wrapped around a roll.

The quality of paper formation indicates the degree of fiber variance in a paper sheet. The measure of the degree of fiber variance takes into account the size and distribution of holes, flock distribution, and dust particle measurements. Generally, in the past this measurement has been accomplished by taking a sheet end product which has been through essentially all the steps of papermaking, and placing that sample sheet on an inspection box with a light source to visually examine transparency distribution of the sheet.

Tissue making comprises many different steps, and each step changes the properties of the tissue sheet. Tissue sheets are commonly processed using techniques such as creping the tissue from a rotating drum, which involves physically scraping the tissue with a blade from a drum to which the tissue is affixed and dried. This creping step greatly softens the "doctor" tissue, and changes dramatically the texture of the tissue. Furthermore, other types of tissues undergo a process of foreshortening and throughdrying known as UCTAD (uncreped through air drying) which includes passing air through the tissue sheet as it rests upon a forming fabric. See, for example, U.S. Pat. Nos. 5,932,068 and 5,772,845 to Farrington et al. and U.S. Pat. No. 6,017,417 to Wendt et al.

One of the difficulties in examining finished tissue products to determine the quality of paper formation and performance of the headbox and forming roll section is that there are so many process steps beyond the headbox (i.e., downstream of tissue formation) that it is difficult to correlate the properties of the final tissue product with the performance of the headbox and slurry handling apparatus at the beginning stages of tissue manufacture. It would therefore be desirable to develop an apparatus and method that can accurately measure the degree of paper formation and fiber variance in a paper sheet while the paper sheet is still wet, i.e., during the process of paper sheet formation. A method and apparatus of determining, in real time, the properties of a wet paper sheet as it is being manufactured on a twin wire forming fabric would be desirable. Further, a method of using information obtained during tissue manufacture to adjust, in real time, the processing variables and parameters which are responsible for the properties of the sheet would be a valuable technique for tissue product developers.

SUMMARY OF THE INVENTION

A method of measuring paper formation is provided in the invention. The method includes a novel way of observing paper formation in real time, while a paper web is forming in the wet end of a papermaking machine.

One method of the invention is directed to depositing a paper slurry upon the upper surface of the forming fabric to form a wet web. Then, light is transmitted from a light source upon the surface of the wet web and reflected from the surface of the wet web. An image is formed corresponding to the pattern of the reflected light. The wet web travels longitudinally through the light pathway to facilitate the impingement of light upon the surface of the wet web.

In some applications of the invention, the light source comprises one or more light lines. Several independent sources of light may be employed, to increase the amount of light available during the line scanning process used by the camera. The camera may advantageously be operated at a speed of at least about 50,000 Hz (i.e., in the range of about 50,000 Hz to about 80,000 Hz). A pattern of pixels is generated in forming the image. A computer having a processor and a monitor may be employed in the practice of the invention.

In many applications, it is preferred that the web comprise a water content of at least about 80% water during the reflecting step. Sometimes, the water content of the wet paper web is about 80–95% and this range of water content has been found to work well under some conditions.

In another aspect of the invention, a system for measuring paper formation in real time is provided. The system is comprised of apparatus for a papermaking process. The apparatus includes a rotating forming fabric having an upper and lower surface. A paper slurry is deposited upon the upper surface of the moving forming fabric to establish a wet paper web. The wet paper web moves at a speed of at least about 4,000 feet per minute. Light is transmitted from a light source upon the surface of the wet paper web. Light reflects from the surface of the wet paper web to a camera. An image is formed that corresponds to the pattern of the reflected light.

In some applications of the invention, the image is displayed upon a computer monitor. The system may include a means by which the camera sends to a computer signals representing light received by the camera. The computer comprises a processor, and the processor compares the signals received with predetermined stored values to determine the degree of deviation of the formation of the paper web from desired paper web formation values.

In this way, it is possible to monitor the physical characteristics of the wet paper web in real time as it is being formed at the wet end of the papermaking machine. It is also possible to modify the parameters that directly affect the physical properties of the wet paper web.

The system, in some embodiments, also may include a processor that transmits feedback signals to apparatus of the papermaking system to modify one or more papermaking parameters in real time, thereby altering the characteristics of the wet web to cause the wet web to conform to desired paper web formation values.

The papermaking parameters that may be modified in a feedback loop of the invention include paper uniformity, sheet water content, stock impingement angle, vacuum box position, and forming fabric tension. Other properties and physical parameters also can be modified to adjust, in real time, the properties of the paper web. In one embodiment, the wet web forms a paper having a weight of less than about 16 lbs/2880 ft$^2$.

The camera employed in the one embodiment of the invention is a line scan camera. The image formed is constructed by scanning lines of the image. Furthermore, the system is provided in which light is transmitted from a light source upon the surface of the wet paper web at an impingement angle of between about 25 and 65 degrees. In some embodiments, the angle is about 45 degrees, but the angle is not believed to be critical for most applications. In at least one application of the invention, a system is provided in which light from the light source travels through at least one focusing lens before impinging upon the surface of the wet web.

BRIEF DESCRIPTION OF THE DRAWINGS

A full and enabling disclosure of the present invention, including the best mode known to one of ordinary skill in the art, is set forth particularly in the specification, including reference to the accompanying figures in which.

DETAILED DESCRIPTION OF THE INVENTION

Reference now will be made to the embodiments of the invention, one or more examples of which are set forth below. Each example is provided by way of explanation of the invention, not as a limitation of the invention. In fact, it will be apparent to those skilled in the art that various modifications and variations can be made in this invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention, which broader aspects are embodied in the exemplary constructions.

The quality of formation is a critical parameter for all grades of paper. In the papermaking industry, the term "formation" refers to the uniformity of distribution of paper fibers in a paper sheet that is formed. Formation in the past has been measured "off line" using processes that study the final paper product after it is dried, rolled, calendered, and pressed into a final sheet after all of the papermaking steps are completed. It has been common in the prior art to adjust and optimize forming tackle and headbox apparatus based upon measurements and observations made on completed paper products after they have been manufactured completely (i.e., finished paper goods). However, for some grades of paper products, such as UCTAD products, an off line measurement is not particularly meaningful, because such measurements are greatly influenced by other process elements such as the rush-transfer step or molding step.

Figure 1:
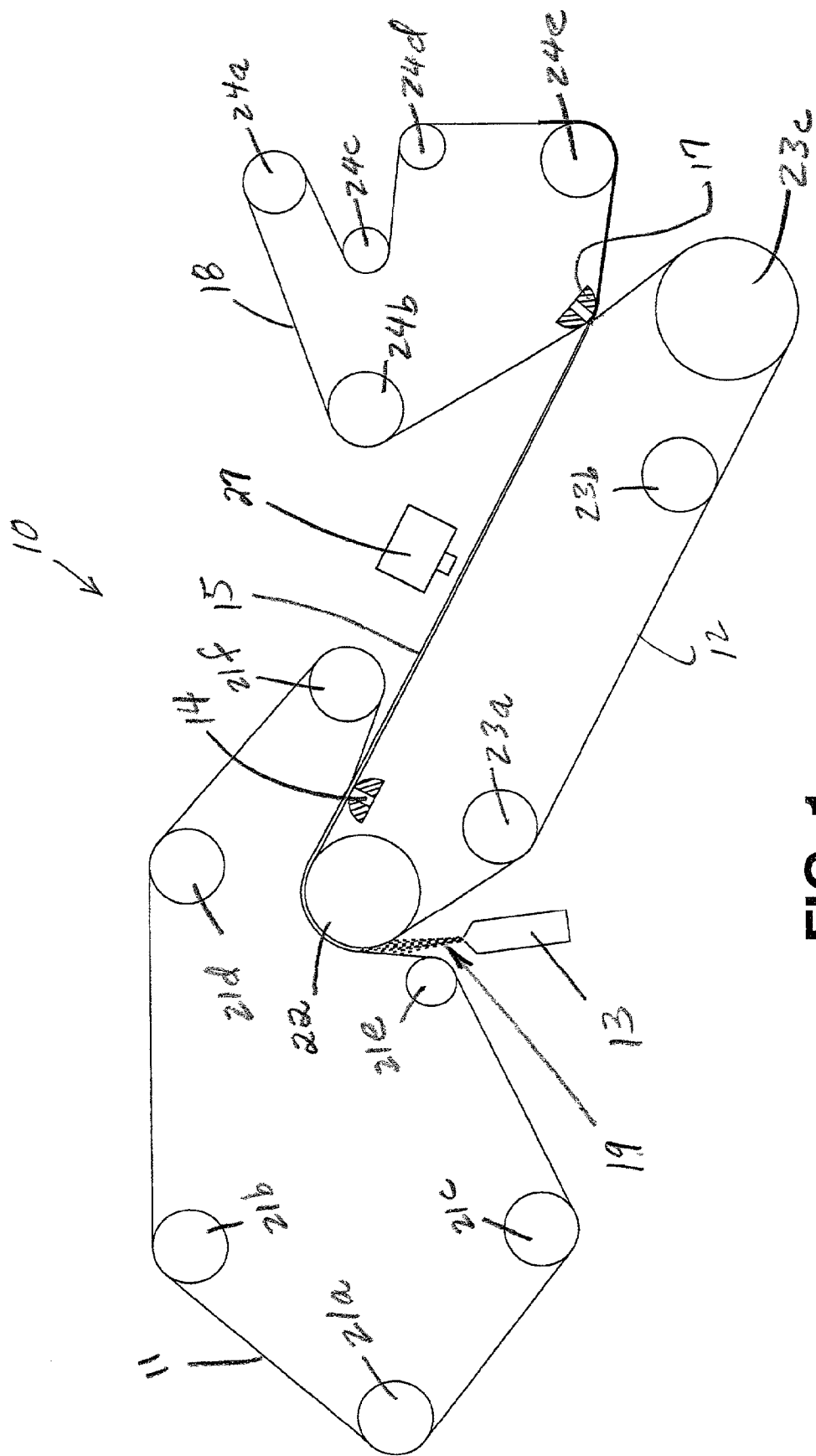
FIG. 1 is an illustration of the headbox and forming fabric orientation relative to the camera used in the practice of the invention.

Turning to FIG. 1, a first portion 10 of the paper forming process using a typical twin wire former is shown. Although the invention may have applicability to essentially any type of web manufacture, including essentially any tope of paper formation process, FIG. 1 is provided to show one specific application of the invention. In FIG. 1, a first forming fabric 11 receives a jet 19 of paper stock (i.e., fiber slurry) from a headbox 13. The slurry is then transformed into a relatively flat sheet, and is drawn to the first forming fabric 11 by a vacuum slot 14. A sheet 15 of paper emerges upon the second forming fabric 12. The, the paper sheet is passed beneath the camera 27, shown schematically in FIG. 1. Then, the sheet 15 travels further along the second forming fabric 12, and may be dried as it travels. Then, the paper is transferred to a third forming fabric 18 near the vacuum slot 17 shown in FIG. 1.

Figure 2:
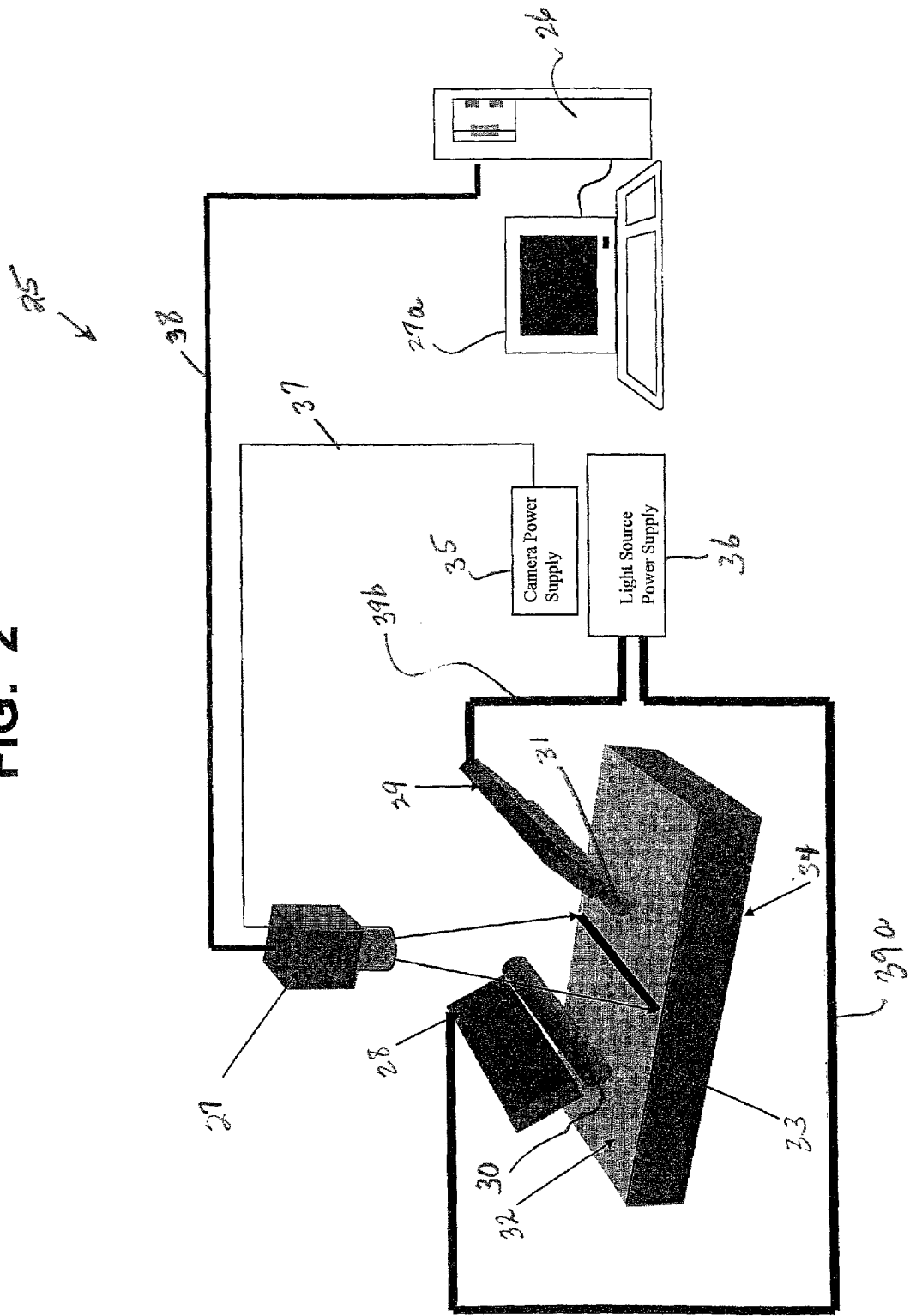
FIG. 2 provides a schematic diagram showing different options and possible applications of the invention which may include multiple light sources and interaction with computing equipment.

In FIG. 2, the web formation measurement system 25 is shown which may in some applications comprise a computer 26 having a camera interface board installed in the computer. One example of a suitable camera interface board that manages the flow of signals representing images is a BIT-FLOW® "Roadrunner" board, which is manufactured by the BITFLOW Corporation. This board is a high speed interface board designed to convert electronic signals which are the output of a high speed line scan camera into images that may be displayed on a monitor or otherwise processed electronically in a software system.

In the process as shown in FIG. 2, a first light source 28 and a second light source 29 may be employed. In some applications, only one light source is used, and in other applications multiple light sources could be employed. In general, there is no limit to the amount and type of light sources that can be employed in the invention. In general, the more light that is used, the better the camera signal, especially at high speed. A first focusing lens 30 and a second focusing lens 31 serve to maximize the effective output of the light sources by directing their flow onto the moving paper sheet 32. The paper sheet 32 rests upon forming fabric 33, which moves underneath the camera at high speed, for example from left to right as shown in FIG. 2. A vacuum box 34, located beneath the forming fabric 33, is provided to pull a vacuum and thereby hold the paper sheet 32 onto the surface of the forming fabric 33.

A camera power supply unit 35 is provided, which supplies power along line 37 to the camera 27. A fiber optic light source and power supply 36 provides light along lines 39a–b to the first light source 28 and second light source 29, respectively.

In some applications of the invention, the computer 26 may provide for an operator to simply push a button or activate software that will provide an image on the monitor 27a. Furthermore, a feedback control loop may be used in some cases to monitor the formation characteristics of the paper, by observing the image. Then an operator may adjust by whatever means are available parameters that affect the paper formation process. In this way, an operator of a papermaking apparatus would have the ability to monitor, in real time, the formation characteristics of paper as it emerges from a headbox and proceeds downstream. One software program that may be particularly useful in the practice of the invention is the SHERLOCK® software which is adapted for visioning and camera equipment. SHERLOCK® software is manufactured and distributed by Imaging Technology, Inc. of Bedford, Mass.

Additional light may be required for a better image. The angle of impingement of the light upon the surface of the moving web is not critical, and in the past angles of impingement of about 45 degrees have been found to work well. In general, the angle of impingement is preferably between about 20–700°, and more preferably between about 25° and about 55° but is not usually critical.

In the early stages of the papermaking process, the forming fabric is supported and driven by a plurality of rolls. The speed at which the fabric or moving web is driven may depend upon the particular application. Forming fabrics may be made of any suitable porous material, such as metal wires or polymeric filaments. However, in the practice of the invention it has been found that a forming fabric which is either black or another dark color (i.e. in which the polymer that makes up the forming fabric has been dyed or colored black or a dark color) is the most advantageous. The reason for using dark or black pigment is that the light reflected from the moving paper web provides a better contrast when the forming fabric under the paper is black. A black or dark forming fabric tends to absorb, and not reflect light, which increases the contrast available using the imaging equipment of the invention.

If the appropriate color or contrast is provided to the forming fabric material, then essentially any suitable fabrics could be used. For example, Albany 84M and 94M available from Albany International of Albany, N.Y. could be used. Other forming fabrics that could be used include the Asten 856, 866, 892, 959, 937 and Asten Synweve Design 274, available from Asten Forming Fabrics, Inc. of Appleton, Wis. The fabric can be a woven fabric as taught in U.S. Pat. No. 4,529,480 to Trokhan. Forming fabrics or felts comprising non-woven base layers may also be useful, including those of Scapa Corporation made with extruded polyurethane foam such as the Spectra Series. Relatively smooth forming fabrics can be used, as well as textured fabrics suitable for imparting texture and basis weight variations to the web. During operation, vacuum slots 14 and 17 are placed in communication with a vacuum device.

One key component of the present invention is that it may be used for papermaking processes comprising paper having a very low basis weight. For example, most flat paper has a basis weight of about 28–32 lbs./2880 ft.$^2$ unit area. On the other hand, facial tissue products are typically of about 7 lbs./2880 ft.$^2$. Typical toilet paper made and sold in the United States has a basis weight of about 15 lbs./2880 ft.$^2$. The invention provided herein could be used for any of the above types of paper, having different basis weights. The invention is not limited to paper having any particular basis weight. However, it has been found that paper with a lower basis weight which has a thinner texture is more translucent, and therefore it is more difficult when manufacturing such paper to determine that the paper formation is occurring properly at the headbox and on the first forming fabric.

In most cases, the image taken by the camera 27 may be from about 10 to about 15 ft. downstream from the headbox, usually only a very short time after initial paper formation. However, a distance of between about 3 and about 30 feet could be used. It has been found that the paper sheet is most correctly imaged, and the invention has the most usefulness, when the water content in the paper sheet is sufficiently high. For example, a paper sheet will not image well, and the formation image taken tends to be less valuable if the water content is too low or too high. In general, the range of water content in the paper that has been found to be most useful in the practice of the invention is between about 80 and about 95% water in the sheet as the sheet passes beneath the camera 27 (see FIG. 2). In many applications, the sheet moves at a speed of at or greater than 4000 ft./min., and a typical speed for the sheet is about 5000 ft./min. This relatively fast speed requires a camera that is capable of taking images extremely rapidly, and forming an image that is not blurred or deformed due to the rapid movement of the paper beneath the lens of the camera 27. For that reason, sophisticated camera technology is required, as further described herein.

The method is capable of measuring formation characteristics at typical operating speeds, which may be as high as 4000 feet per minute, or greater. While the methods and apparatus of this invention are particularly useful in connection with the UCTAD process of tissue manufacture, the method also has application in many other grades of paper, including the creped tissue processes.

In the practice of the invention, at least two significant problems in paper formation and manufacture are addressed. First, prior art methods of observing tissue formation in a laboratory analysis long after the product has been formed and completed is typically too late to change the process which resulted in the tissue manufacture. That is, because in the past most methods of paper formation analysis were not conducted during production runs, but instead after tissue was manufactured, it was not possible to observe or affect the physical parameters and headbox characteristics that could be altered to provide a sheet having more desirable formation characteristics. The ability to measure performance in real time during tissue manufacture affords the opportunity to: (1) receive more reliable test data, and (2) monitor or change such characteristics in real time during manufacture.

Creping and other downstream processes (such as rush-transfer) greatly affect the physical properties of the sheet ultimately produced. Therefore, laboratory analysis which is conducted after these physical changes is not as accurate in examining the stages of formation because the paper or tissue is significantly altered by these subsequent processing steps. In the practice of the invention, it is possible to more accurately study the process of formation by examining the tissue prior to rush-transfer or creping steps.

For grades of paper such as UCTAD (Uncreped Through Air Dried), this off-line measurement of formation is not very meaningful since process conditions such as dewatering, pressing, rush-transfer, molding, drying, and calendering can mask the true formation of the sheet. In order to obtain valuable formation information, a method of analyzing formation on the we end of the machine is needed.

This method for formation analysis of the invention has the potential to become very valuable for all grades of paper due to the formation information that can be received on-line directly after the headbox, where the actual formation of the sheet occurs. This method of analyzing wet end formation allows for many immediate changes to be made to optimize formation parameters such as headbox position, impingement angle, breast roll positions, vacuum box levels and positions, jet/wire ratio, furnish, forming consistency, freeness, fiber split, and other parameters known by persons of skill in the art.

The following terms apply in the practice of the invention:

Headbox position generally refers to the elevation and angle of the headbox affecting placement of the stock jet on the forming fabrics. Impingement angle generally refers to the angle at which the fabric impinges on the second forming fabric. This is affected by the headbox position and fabric positions.

The Vacuum box position, in a suction forming roll, is the position of the vacuum box inside the drilled shell that can be rotated relative to the point of jet impingement, thus adjusting the place where vacuum dewatering starts to occur. The Vacuum box level generally refers to the level used inside the suction roll affecting the intensity of dewatering, as well as the relative drainage rate through the No. 1 vs. the No. 2 forming fabrics. The Jet-to-Wire ratio is generally referred to as the velocity ratio between the jet of stock exiting the headbox and the fabric on which the sheet is formed. This ratio influences the quality of formation, as well as the tensile ratio of the sheet.

In general, Forming consistency affects the level of dilution in the stock slurry and dictates the rate at which water must be drained in the forming process. It can be controlled by opening and closing the slice of the headbox to allow more or less water flow, without changing the dry fiber flow. The term "furnish" generally refers to the type of fibers used to make the sheet. Some fibers drain more rapidly than others. In general, Breast roll position affects both the fabric impingement angle, as well as the free jet length, (i.e. the distance the stock jet travels from the headbox before touching a fabric surface).

In most cases, the process conditions affecting formation include machine speed, furnish blend (mix of fiber types), stock freeness (ease of drainage), and basis weight. Furthermore, potential response variables include jet impingement angle, breast roll position, vacuum level, vacuum box position, jet-to-wire ratio, and forming consistency.

It is important to produce the contrast needed to observe the fiber distribution in the wet sheet. This contrast can be achieved by forming the fabric using black or dark chutes and white, light or translucent warps. In general, black or dark fabric colors are preferred in the invention to provide the degree of contrast needed to observe the light reflection as described below. One forming fabric that has been used is a gray Appleton Mills X-shed fabric with black top chutes. However, some fabrics, including the Appleton Mills X-shed fabric with black top chutes, may not provide the desired amount of color contrast. If it is not dark enough to achieve the contrast that is required, it may be dyed black. The problem may be alleviated by providing black or dark chutes on the top and bottom of the fabric. Certainly, it is believed that other fabrics could work as well.

In the practice of the invention, formation testing typically is accomplished using a high speed (50,000–80,000 Hz) line scan camera mounted above the sheet on a forming or carrying fabric. One camera that may be used in the practice of the invention is a camera known as the PIRANHA® high speed camera manufactured by Dalsa, Inc. (i.e. see www.dalsa.com). A camera model that may be employed in the invention CT-P1 camera having 1024 resolution, with 10 micrometers square pixels. This camera includes four outputs for a maximum line rate of 79 k Hz. The camera provides an 8 bit data at 25 MHz per output, for a total pixel rate of 100 MHz. The camera provides exposure control and anti-blooming and includes a data format EIA-644 (LVDS). The PIRANHAS CT-P1 Line Scan camera provides digital video with responsivity at 25 MHz per output on 4 outputs. This system provides connecting circuit modules through standardized buses to build a high performance modular camera using reliable and interchangeable parts. The PIRANHA® CT-P1 is suited for applications including high performance documenting scanning, optical character recognition, and the like. The sensor employed in the camera provides a linear array consisting of a line of photo elements, each with a photosensitive area of about 10 µm×10 µm and a center to center spacing of 10 µm. The camera further provides an adapter for C-mount or F-mount lenses, depending on the sensor resolution. In general, the standard PIRANHA® cameras require only one input signal to operate. With regard to output signals, such signals indicate when the data is valid, thereby facilitating the clocking of the data from the camera to the acquisition system. It is understood that any camera having operating parameters similar to those described herein may be used.

When using computers in conjunction with machine vision software, such as SHERLOCK®, to acquire images from high-speed processes, inspection tools may be placed on these images to analyze or extract information for process control. This information can be communicated from the computer to the papermaking machine using numerous different types of output technology including but not limited to analog and digital output cards. The papermaking machine controls would make these transmitted feedback signals and adjust formation parameters such as impingement angle, vacuum box levels and positions, jet/wire ratio, and other parameters known by persons of skill in the art. As these parameters are adjusted the formation of the tissue sheet would change with the change detected by the vision system thereby completing the feedback control loop.

Numerous types of light sources can be used in the practice of the invention. One light source that has been found to be particularly useful is a product called a Fostec Lightlines® which are manufactured by the Fostec Corporation. Fostec fiber optic light transmitting sources may provide either increased light intensity, or may in some cases project a strip of light. In the practice of the invention, it is possible to provide a crisp line of light without the usual stray light that is generally undesirable. One, two or more light sources may be employed.

The apparatus and methods of the invention are applicable over a wide range of wet web materials, including cellulosic and non-cellulosic webs. Furthermore, carrying media such as woven and non-woven belts, papermaking fabrics, and wet felts provide adequate contrast between the web and the carrying media. An adequate contrast is required in order to obtain the images necessary in the practice of the invention.

One benefit of a wet end formation analysis upon a sheet is that it facilitates a direct measurement, including feedback and optimization of the forming parameters such as headbox set-up, impingement angle, forming roll and breast roll positions, vacuum box levels and positions, paper uniformity, sheet water content, stock impingement angle, vacuum box position, and forming fabric tension.

Because the paper to be inspected during manufacture is of considerable size (for example may be 220 inches wide) a portion of the paper may be viewed, and therefore imaged, by the camera as a sample (i.e. 10 in.×10 in. or more) to represent many useful features of the paper that include an apparent steady area or area where quality of the entire paper can be judged by inspecting one representative area.

During measurement, adjustment is made such that an adequate quantity of transmitted light may be obtained from the light source according to the thickness of the paper. The adjustment to the aperture of the camera is performed, and a signal representative of an image entering the camera is obtained.

It is understood by one of ordinary skill in the art that the present discussion is a description of exemplary embodiments only, and is not intended as limiting the broader aspects of the present invention, which broader aspects are embodied in the exemplary constructions The invention is shown by example in the appended claims.

What is claimed is:

1. A method of measuring paper formation or distribution in a papermaking process, comprising:
   (a) providing a forming fabric;
   (b) depositing a paper slurry upon the forming fabric to form a wet web;

(c) transmitting light from a light source upon a first side of the wet web;

(d) reflecting the light from the first side of the wet web to a camera, thereby forming a pattern of reflected light;

(e) forming a visual image of the wet web corresponding to the pattern of the reflected light; and (f) utilizing the pattern of reflected light to which the visual image corresponds to control paper formation in the wet web.

2. The method of claim 1 further comprising the step of moving the wet web longitudinally through the light pathway to facilitate the impingement of light upon the surface of the wet web.

3. The method of claim 1 in which the light source comprises a light line.

4. The method of claim 1 in which there are at least two independent sources of light.

5. The method of claim 1 in which the step of forming an image further comprises receiving the reflected light in a line scan camera.

6. The method of claim 5 in which the camera operates at a speed of at least about 50,000 Hz.

7. The method of claim 6 in which pixels are generated in forming the image.

8. The method of claim 7 in which the web comprises a water content of at least about 80% water during the reflecting step.

9. The method of claim 8 in which the web comprises a water content of between about 80% to about 95%.

10. The method of claim 2 in which the wet web moves at a speed of at least about 4000 feet/minute.

11. The method of claim 10 in which the forming fabric is black in color.

12. The method of claim 1, wherein the forming fabric has a dark color.

13. A method for measuring paper formation in real time on a papermaking process, comprising:
   (a) providing a rotating forming fabric having an upper and lower surface;
   (b) depositing a paper slurry upon the upper surface of the forming fabric to establish a wet paper web, the wet paper web moving at a speed of at least about 4000 feet per minute;
   (c) transmitting light from a light source upon the upper surface of the wet paper web;
   (d) reflecting light from the upper surface of the wet paper web to a camera thereby forming a pattern of reflected light;
   (e) forming a visual image of the wet paper web corresponding to the pattern of the reflected light; and
   (f) utilizing the pattern of reflected light to which the visual image corresponds to measure paper formation in the wet web.

14. The method of claim 13 in which the image is displayed upon a computer monitor.

15. The method of claim 13 in which the camera sends to a computer signals representing light received by the camera, further wherein the computer comprises a processor, whereby the processor of the computer compares said signals with predetermined stored values to determine the degree of deviation of the formation of the paper web from desired paper web formation values.

16. The method of claim 15 in which the processor is configured to adjust one or more papermaking parameters in real time to alter the characteristics of the wet web to cause the wet paper web to conform to desired paper web formation values.

17. The method of claim 16 in which the papermaking parameters comprise the group consisting of:
   a) paper uniformity,
   b) sheet water content,
   c) stock impingement angle,
   d) vacuum box position, and
   e) forming fabric tension.

18. The method of claim 13 in which the wet web forms a paper having a weight of less than about 16 lbs/2880 ft$^2$.

19. The method of claim 13 in which the camera is a line scan camera, and the image formed is constructed by scanning lines of the image.

20. The method of claim 13 in which the light is transmitted from a light source upon the surface of the wet paper web at an impingement angle of between about 25 and 65 degrees.

21. The method of claim 13 in which more than one light source is employed to transmit light.

22. The method of claim 13 in which a vacuum box is employed to take water from the wet web while the wet web is moving along the surface of the rotating forming fabric.

23. The method of claim 13 in which light from the light source travels through at least one focusing lens before impinging upon the surface of the wet web.

24. The method of claim 13, wherein the forming fabric has a dark color.

25. The method of claim 13, wherein the forming fabric comprises a black color.

26. A method of measuring formation or distribution in a web forming process comprising the steps of:
   providing a forming fabric;
   depositing a slurry of fibers upon the forming fabric to form a wet web;
   emitting light from a light source upon a first side of the wet web;
   detecting reflected light from the wet web by a camera positioned in communication with the first side of the web, the camera forming a pattern of reflected light;
   forming a visual image of the wet web corresponding to the pattern of the reflected light; and
   based upon the formed visual image, adjusting one or more web making parameters in order to improve the web formation.

27. A method as defined in claim 26, wherein the web making parameter comprises machine speed, fiber furnish blend, stock freeness, basis weight, stock impingement angle, vacuum box position, or forming fabric tension.

\* \* \* \* \*